US00PP15980P2

(12) United States Plant Patent
van Rijn

(10) Patent No.: US PP15,980 P2
(45) Date of Patent: Sep. 20, 2005

(54) ***ANTHURIUM* PLANT NAMED 'RIJN200002'**

(50) Latin Name: *Anthurium andreanum*
Varietal Denomination: Rijn200002

(75) Inventor: Leonardus W. B. M. van Rijn, DeLier (NL)

(73) Assignee: Rijnplant B.V., Schipluiden (NL)

( * ) Notice: Subject to any disclaimer, the term of this patent is extended or adjusted under 35 U.S.C. 154(b) by 26 days.

(21) Appl. No.: 10/917,146

(22) Filed: Aug. 12, 2004

(51) Int. Cl.[7] ..... A01H 5/00

(52) U.S. Cl. ..... Plt./365

(58) Field of Search ..... Plt./365

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Anthurium* plant named 'Rijn200002', characterized by its upright and somewhat outwardly spreading plant habit; large, durable and dark green-colored leaves; red-colored spathes with pale yellow-colored spadices that are positioned above and beyond the foliage on strong and erect scapes; freely flowering habit; and good inflorescence longevity.

1 Drawing Sheet

Botanical classification/cultivar designation: *Anthurium andreanum* cultivar Rijn200002.

BACKGROUND OF THE INVENTION

The present invention relates to a new and distinct cultivar of *Anthurium* plant, botanically known as *Anthurium andreanum*, and hereinafter referred to by the name 'Rijn200002'.

The new *Anthurium* is a product of a planned breeding program conducted by the Inventor in Schipluiden, The Netherlands. The objective of the program is to create and develop new freely clumping and freely flowering *Anthurium* cultivars with strong roots, dark green-colored leaves, attractive spathe color, and good inflorescence longevity.

The new *Anthurium* originated from a cross by the Inventor on or about Jan. 7, 1998 of a proprietary *Anthurium andreanum* selection code number 96-003 as the female, or seed, parent with a proprietary *Anthurium andreanum* selection code number 90-090 as the male, or pollen, parent. The cultivar Rijn200002 was discovered and selected by the Inventor as a plant within the progeny of the stated cross in a controlled environment in De Lier, The Netherlands in January, 2000.

Asexual propagation of the new cultivar by meristem culture in a laboratory in Belgium has shown that the unique features of this new *Anthurium* plant are stable and reproduced true to type in successive generations of asexual propagation.

BRIEF SUMMARY OF THE INVENTION

The new *Anthurium* has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Rijn200002. These characteristics in combination distinguish 'Rijn200002' as a new and distinct cultivar:

1. Upright and somewhat outwardly spreading plant habit.
2. Large, durable and dark green-colored leaves.

3. Red-colored spathes with pale yellow-colored spadices that are positioned above and beyond the foliage on strong and erect scapes.
4. Freely flowering habit.
5. Good inflorescence longevity.

Plants of the new *Anthurium* can be compared to plants of the female parent, the selection 96-003. In side-by-side comparisons conducted in De Lier, The Netherlands, plants of the new *Anthurium* differed from plants of the selection 96-003 in the following characteristics:

1. Plants of the new *Anthurium* had much larger leaves than plants of the selection 96-003.
2. Plants of the new *Anthurium* were bushier than plants of the selection 96-003.
3. Spathe color of plants of the new *Anthurium* was red whereas spathe color of plants of the selection 96-003 was pink.

Plants of the new *Anthurium* can be compared to plants of the male parent, the selection 90-090. In side-by-side comparisons conducted in De Lier, The Netherlands, plants of the new *Anthurium* differed from plants of the selection 90-090 in the following characteristics:

1. Plants of the new *Anthurium* had more durable leaves than plants of the selection 90-090.
2. Plants of the new *Anthurium* had larger leaves than plants of the selection 90-090.

Plants of the new *Anthurium* can also be compared to plants of the cultivar Red King, disclosed in U.S. Plant Pat. No. 13,381. In side-by-side comparisons conducted in De Lier, The Netherlands, plants of the new *Anthurium* differed from plants of the cultivar Red King in the following characteristics:

1. Plants of the new *Anthurium* had much larger and darker green-colored leaves than plants of the cultivar Red King.
2. Plants of the new *Anthurium* had darker red-colored spathes than plants of the cultivar Red King.
3. Spathe color of plants of the new *Anthurium* developed faster than spathe color of plants of the Red King.

BRIEF DESCRIPTION OF THE PHOTOGRAPH

The accompanying colored photograph illustrates the overall appearance of the new *Anthurium*, showing the colors as true as it is reasonably possible to obtain in colored reproductions of this type. Colors in the photograph may differ slightly from the color values cited in the detailed botanical description which accurately describe the colors of the new *Anthurium*.

The photograph comprises a side perspective view of a typical flowering plant of the cultivar Rijn200002 that was about one year-old.

DETAILED BOTANICAL DESCRIPTION

In the following description, color references are made to The Royal Horticultural Society Colour Chart, 1995 Edition, except where general terms of ordinary dictionary significance are used. The following observations and measurements describe one-year old plants grown in 17 to 22-cm containers in De Lier, The Netherlands, in a glass greenhouse with an average day temperature of 23° C., an average night temperature of 21° C. and average light level of 6 kilolux.

Botanical classification: *Anthurium andreanum* cultivar Rijn200002.

Parentage:

*Female parent.*—Proprietary *Anthurium andreanum* selection code number 96-003, not patented.

*Male parent.*—Proprietary *Anthurium andreanum* selection code number 90-090, not patented.

Propagation:

*Method.*—By meristem culture.

*Time to initiate roots on a meristem-cultured plant.*—About four weeks at 24° C.

*Time to develop roots on a meristem-cultured plant.*—About nine months at 20 to 24° C.

*Root description.*—Primary roots, thick and fleshy and dark pink to cream in color; lateral roots, thick and abundant.

Plant description:

*Plant shape.*—Upright and somewhat outwardly spreading plant habit, inverted triangle, symmetrical.

*Growth habit.*—Moderately clumping. Appropriate for 17 to 35-cm containers. Vigorous.

*Plant height.*—About 75 to 90 cm.

*Plant diameter and spread.*—About 65 cm.

*Crop time.*—About 10 months are usually required from planting of young plants to finished plants in a 17-cm container.

*Foliage description.*—Quantity per plant: About 30. Length: About 27 to 47 cm. Width: About 16 to 27 cm. Shape: Cordate. Apex: Apiculate. Base: Auriculate; lobes not overlapping. Margin: Entire. Texture: Leather; glabrous. Venation pattern: Pinnate. Color: Developing leaves, upper surface: Darker than 137A. Developing leaves, lower surface: Darker than 144A. Fully expanded leaves, upper surface: Darker than 147A. Fully expanded leaves, lower surface: Darker than 146A. Venation, upper and lower surfaces: Darker than 144A. Petiole: Length: About 20 to 38 cm. Geniculum length: About 2 to 3 cm. Geniculum color: 144A. Petiole and geniculum color: 144A.

Inflorescence description:

*Inflorescence arrangement.*—Spathes with spadices held above and beyond the foliage. Flowering structures arise from leaf axils. Freely and continuous flowering year-round; typically more than twelve inflorescences per plant at one time.

*Inflorescence longevity.*—Inflorescences last about six weeks under winter conditions and about three months under summer conditions; persistent.

*Spathe.*—Length: About 14 to 18 cm. Width: About 11 to 15 cm. Shape: Cordate. Apex: Aristate. Base: Auriculate, lobes not overlapping. Margin: Entire. Texture: Leathery; glabrous; moderate blistering. Color: When opening, front and back surfaces: 46A; towards the base, 183A; glossy. Fully developed, front surface: 46A; glossy. Fully opened, back surface: 53A; glossy.

*Spadix.*—Length: About 7 to 9 cm. Diameter: About 1.2 cm. Shape: Columnar. Cross section: Rounded. Longitudinal axis: Erect. Color: Immature: 143A. Mature: 11D.

*Flowers.*—Quantity per spadix: Numerous, about 400. Shape: Rounded. Diameter: About 1 mm, maximum.

*Reproductive organs.*—Androecium: Pollen color: Close to 158B. Gynoecium: Stigma shape: Ovoid.

*Scape.*—Length: About 40 to 60 cm. Aspect: Strong and erect. Color: 144A.

*Seed/fruit.*—Seed/fruit development on plants of the new *Anthurium* has not been observed.

Disease/pest resistance: Under commercial conditions, plants of the new *Anthurium* have not been observed to be resistant to pathogens or pests common to *Anthurium*.

Temperature tolerance: Plants of the new *Anthurium* have been observed to tolerate temperatures from about 14 to about 35 to 36° C.

It is claimed:

1. A new and distinct cultivar of *Anthurium* plant named 'Rijn200002', as illustrated and described.

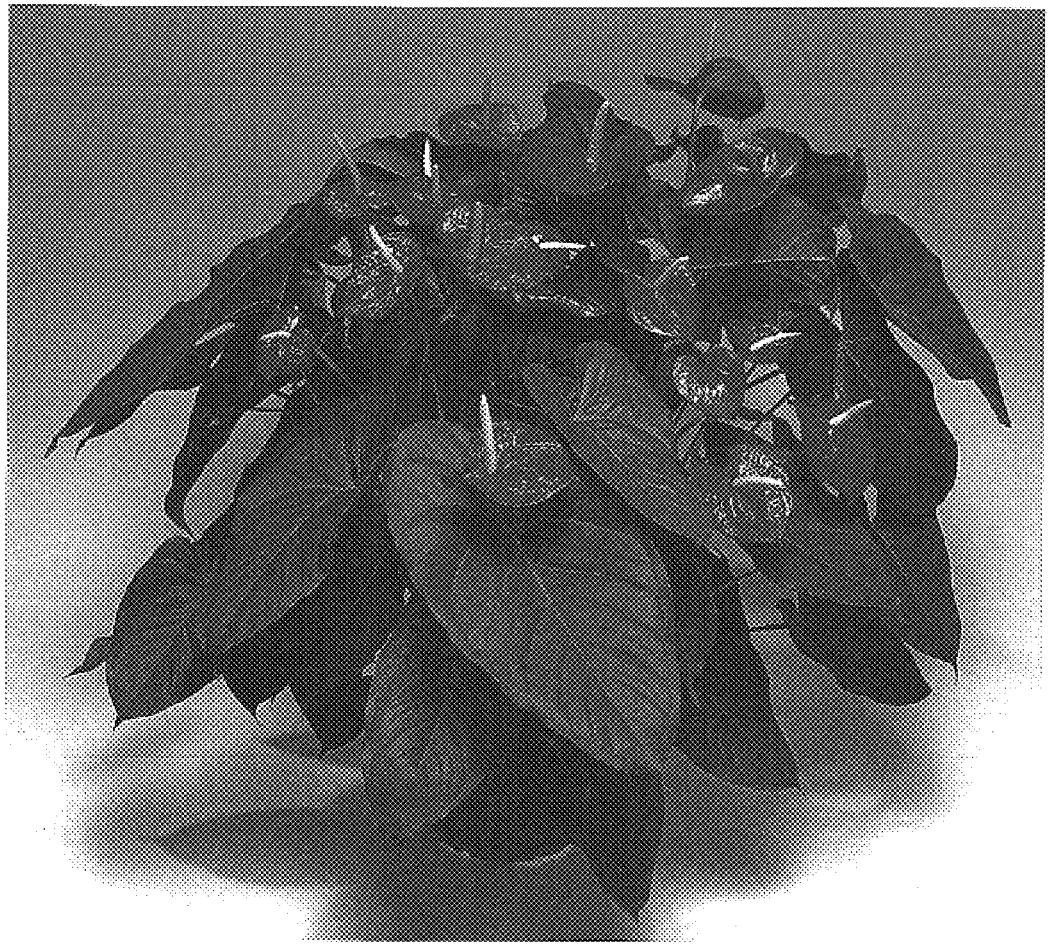

* * * * *